(12) United States Patent
Corbin et al.

(10) Patent No.: US 10,737,036 B2
(45) Date of Patent: Aug. 11, 2020

(54) HOUSING AND CAP FOR MEDICAL INJECTOR

(71) Applicant: Becton Dickinson France S.A.S., Le Pont-de-Claix (FR)

(72) Inventors: Jean-Yves Corbin, Le Fresne Camilly (FR); Maxime Vaupres, Grentheville (FR)

(73) Assignee: Becton Dickinson France S.A.S., Le Pont-de-Claix (FR)

( * ) Notice: Subject to any disclaimer, the term of this patent is extended or adjusted under 35 U.S.C. 154(b) by 621 days.

(21) Appl. No.: 15/372,591

(22) Filed: Dec. 8, 2016

(65) Prior Publication Data

US 2017/0157331 A1    Jun. 8, 2017

Related U.S. Application Data

(60) Provisional application No. 62/264,501, filed on Dec. 8, 2015.

(51) Int. Cl.
| | |
|---|---|
| *A61M 5/315* | (2006.01) |
| *A61M 5/178* | (2006.01) |
| *A61M 5/31* | (2006.01) |
| *A61M 5/32* | (2006.01) |

(52) U.S. Cl.
CPC ........ *A61M 5/31576* (2013.01); *A61M 5/178* (2013.01); *A61M 5/3137* (2013.01); *A61M 5/3148* (2013.01); *A61M 5/3213* (2013.01); *A61M 5/3157* (2013.01); *A61M 5/31501* (2013.01); *A61M 5/3202* (2013.01); *A61M 5/3204* (2013.01); *A61M 2005/3139* (2013.01)

(58) Field of Classification Search
CPC .............. A61M 5/2033; A61M 5/3202; A61M 5/3204; A61M 5/326; A61M 5/20; A61M 5/24; A61M 5/3213; A61M 5/3234; A61M 5/158; A61M 5/31511; A61M 5/322; A61M 5/002; A61J 1/2096; A61J 1/2089
See application file for complete search history.

(56) References Cited

U.S. PATENT DOCUMENTS

| | | | |
|---|---|---|---|
| 2,860,635 A * | 11/1958 | Wilburn | A61M 5/3202 604/190 |
| D239,021 S | 3/1976 | D'Alo | |
| 4,365,626 A | 12/1982 | House | |
| 4,832,695 A | 5/1989 | Rosenberg et al. | |
| 4,929,232 A | 5/1990 | Sweeney et al. | |

(Continued)

FOREIGN PATENT DOCUMENTS

| | | |
|---|---|---|
| EP | 2923716 A1 | 9/2015 |
| WO | 03051423 A2 | 6/2003 |

(Continued)

*Primary Examiner* — Manuel A Mendez
(74) *Attorney, Agent, or Firm* — The Webb Law Firm (57) ABSTRACT

A medical injector is disclosed. The medical injector includes an upper guard housing having a gripping component, a lower guard housing defining a reservoir, and a stopper engaged with a portion of the upper guard housing, the stopper being slidably disposed within the reservoir and sized to provide sealing engagement with an interior sidewall of the lower guard housing. The upper guard housing at least partially surrounds the lower guard housing and is moveable relative to the lower guard housing to advance the stopper through the reservoir.

18 Claims, 8 Drawing Sheets

(56) References Cited

U.S. PATENT DOCUMENTS

| | | |
|---|---|---|
| D337,157 S | 7/1993 | Ortiz |
| D375,788 S | 11/1996 | Potts et al. |
| D380,262 S | 6/1997 | Van Funderburk et al. |
| 5,647,849 A | 7/1997 | Kalin |
| D427,308 S | 6/2000 | Zinger |
| D473,646 S | 4/2003 | Baillargeon et al. |
| 6,582,397 B2 | 6/2003 | Alesi et al. |
| D483,487 S | 12/2003 | Harding et al. |
| D486,225 S | 2/2004 | Gay, III |
| D492,774 S | 7/2004 | Cindrich et al. |
| D497,990 S | 11/2004 | Jutila |
| D505,200 S | 5/2005 | Simpson et al. |
| 7,059,327 B2 | 6/2006 | Worthington |
| D605,755 S | 12/2009 | Baxter et al. |
| D607,558 S | 1/2010 | Abry et al. |
| D629,510 S | 12/2010 | Grunhut |
| D633,199 S | 2/2011 | MacKay et al. |
| D637,713 S | 5/2011 | Nord et al. |
| D642,261 S | 7/2011 | York et al. |
| D655,000 S | 2/2012 | Mirigian |
| D655,017 S | 2/2012 | Mosler et al. |
| D679,008 S | 3/2013 | Schroeder et al. |
| D681,230 S | 4/2013 | Mosler et al. |
| D702,343 S | 4/2014 | Dale et al. |
| D702,835 S | 4/2014 | Vinchon |
| D709,753 S | 7/2014 | Guala |
| 8,858,507 B2 | 10/2014 | Nielsen et al. |
| 8,858,508 B2 * | 10/2014 | Lavi .................. A61M 5/326 604/110 |
| D718,439 S | 11/2014 | Woehr et al. |
| D738,494 S | 9/2015 | Kashmirian |
| D750,239 S | 2/2016 | Pappalardo |
| D750,258 S | 2/2016 | Crossley |
| D750,779 S | 3/2016 | Ahluwalia et al. |
| D751,192 S | 3/2016 | She et al. |
| D755,966 S | 5/2016 | Ahluwalia et al. |
| D755,967 S | 5/2016 | Ahluwalia et al. |
| D757,258 S | 5/2016 | Weibhaupt et al. |
| D757,935 S | 5/2016 | Solingen et al. |
| D760,891 S | 7/2016 | Nakamura et al. |
| D761,422 S | 7/2016 | Row et al. |
| D765,241 S | 8/2016 | Holland |
| D768,850 S | 10/2016 | Rozwadowski et al. |
| D768,851 S | 10/2016 | Rozwadowski et al. |
| 2001/0044606 A1 | 11/2001 | Inkpen et al. |
| 2004/0133172 A1 | 7/2004 | Wilkinson |
| 2004/0210197 A1 | 10/2004 | Conway |
| 2007/0129686 A1 | 6/2007 | Daily et al. |
| 2008/0228147 A1 | 9/2008 | David-Hegerich et al. |
| 2009/0312705 A1 | 12/2009 | Grunhut et al. |
| 2011/0092915 A1 | 4/2011 | Olson et al. |
| 2012/0029439 A1 | 2/2012 | Hudson et al. |
| 2013/0085453 A1 | 4/2013 | Manke et al. |
| 2015/0045729 A1 | 2/2015 | Denzer et al. |
| 2015/0165129 A1 | 6/2015 | Row et al. |
| 2015/0258283 A1 * | 9/2015 | Imai .................. A61M 5/3293 604/195 |
| 2016/0144132 A1 | 5/2016 | Scanlon |
| 2016/0193428 A1 | 7/2016 | Perthu |
| 2017/0014578 A1 | 1/2017 | Bunch |

FOREIGN PATENT DOCUMENTS

| | | |
|---|---|---|
| WO | 2005025636 A2 | 3/2005 |
| WO | 2014150201 A1 | 9/2014 |
| WO | 2014154498 A1 | 10/2014 |
| WO | 2015014363 A2 | 2/2015 |
| WO | 2015073740 A2 | 5/2015 |
| WO | 2015105511 A1 | 7/2015 |
| WO | 2015123096 A1 | 8/2015 |

* cited by examiner

HOUSING AND CAP FOR MEDICAL INJECTOR

CROSS REFERENCE TO RELATED APPLICATIONS

This application claims the benefit of U.S. Provisional Application No. 62/264,501 filed Dec. 8, 2015, the disclosure of which is incorporated herein by reference in its entirety.

BACKGROUND OF THE INVENTION

Field of the Disclosure

The present disclosure relates generally to medical injector devices for delivery of a fluid or liquid medicament. More particularly, the present disclosure relates to a housing and a safety cap for a medical injector device or a syringe.

Description of the Related Art

Medical injectors and syringes are well known in the prior art. Medical injectors may include auto-injectors and pen injectors which are capable of delivering selected doses of fluids including liquid medicaments or vaccinations to a patient. Medical injectors typically are configured to receive a standard pre-filled glass or plastic syringe tipped with an injection needle. These devices may include a drive member for advancing a plunger into a syringe barrel to expel a liquid medicament out through the needle. The required manipulation of a standard prior art hypodermic syringe can be inconvenient, particularly where the injection is self-administered in a public environment, and many medication delivery pens, pen injectors, or other self-injectors have been developed to facilitate self-administration of injections.

In order to maintain sterility prior to use and to reduce the risk of incurring an accidental needle-stick, protection of the needle tip is important. Medical injectors are typically supplied with a rubber or plastic cap which guards the needle prior to use. Immediately prior to use, the user must remove the protective cap from the injector, such as by using the cap protector of the present invention.

SUMMARY OF THE INVENTION

In accordance with an embodiment of the present invention, a medical injector includes an upper guard housing having a gripping component, a lower guard housing defining a reservoir, and a stopper engaged with a portion of the upper guard housing, the stopper being slidably disposed within the reservoir and sized to provide sealing engagement with an interior sidewall of the lower guard housing. The upper guard housing at least partially surrounds the lower guard housing and is moveable relative to the lower guard housing to advance the stopper through the reservoir.

In one embodiment, the gripping component may be concave or convex with respect to an exterior surface of the upper guard housing. For example, the gripping component may include a plurality of gripping ribs extending at least partially about the exterior surface of the upper guard housing.

A window is defined through a portion of the upper guard housing for viewing the stopper during use. To aid in viewing the stopper the lower guard housing may be formed from a transparent material.

The medical injector may further include a flange provided adjacent a distal end of the upper guard housing and a flange provided on a portion of the lower guard housing. Distal movement of the upper guard housing relative to the lower guard housing is limited by engagement of the flange of the lower guard housing and the flange of the upper guard housing.

The medical injector may further include a needle having a sharpened first end and a second end in communication with the reservoir. A cap may cover the sharpened first end of the needle and a liquid medicament may be disposed within the reservoir.

In one embodiment, a cross section of the upper guard housing taken perpendicular to a longitudinal axis of the upper guard housing is generally elliptical in shape.

In accordance with another embodiment of the present invention a handle for use with a medical injection device for dispelling a fluid from the medical injection device is provided. The handle includes a handle body having a proximal end, a distal end, and an interior wall defining a cavity within the distal end of the handle body, a stopper assembly receivable at least partially within the cavity, and a gripping component provided on an external surface of the handle body. The handle body is adapted to be mounted over a housing defining a reservoir and axially slidable over the housing to advance the stopper through the reservoir.

In one embodiment, the gripping component includes a plurality of ribs being convex with respect to the handle body. A window is defined through a portion of the handle body. The handle body may have a non-circular cross section, for example, the cross section may be substantially elliptical in shape.

In one embodiment, a flange is provided adjacent the distal end of the handle body. The flange may include a first wing flange extending from the handle body in a first direction and a second wing flange extending from the handle body in a second direction, such that the first direction is generally opposite the second direction. The first and second wing flanges may each comprise a tapered proximally directed surface.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

In the following discussion, "distal" refers to a direction generally toward an end of a medical injector adapted for contact with a patient and/or engagement with a separate device, and "proximal" refers to the opposite direction of distal, i.e., away from the end of a medical injector adapted for engagement with the separate device. For purposes of this disclosure, the above-mentioned references are used in the description of the components of a medical injector in accordance with the present disclosure.

FIGS. 1-10 illustrate an exemplary embodiment of the present disclosure. Referring to FIGS. 1-10, in one embodiment, a medical injector 10 of the present disclosure includes an upper guard housing component 100 and a lower guard housing component 102. The upper guard housing component 100 surrounds the lower guard housing component 102 and is slidable relative thereto. The upper guard housing 100 provides an enlarged gripping component 110 to aid a user in handling the medical injector 10.

Figure 1:
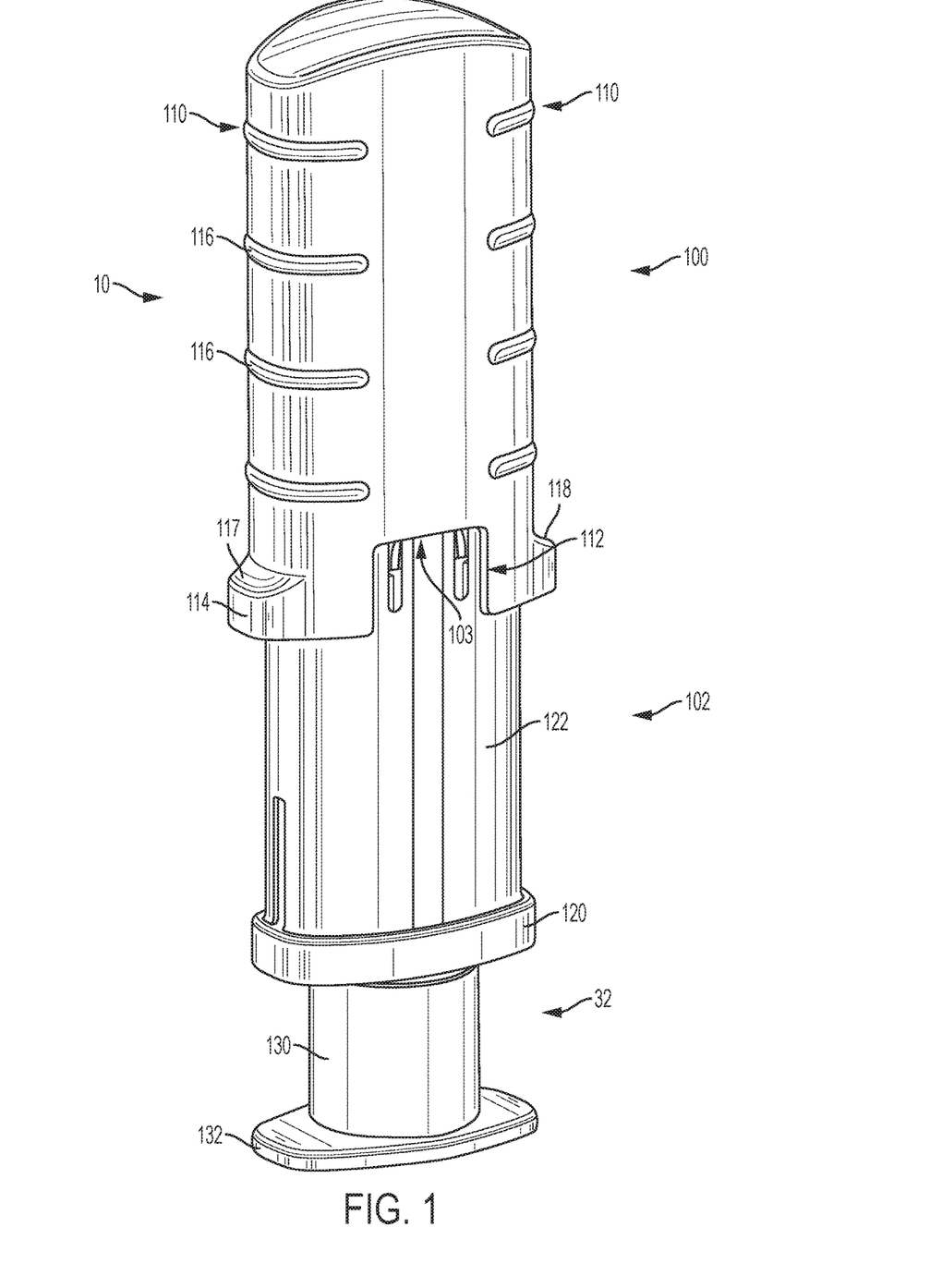
FIG. 1 is a perspective view of a medical injector in accordance with an embodiment of the present invention.
Figure 2:
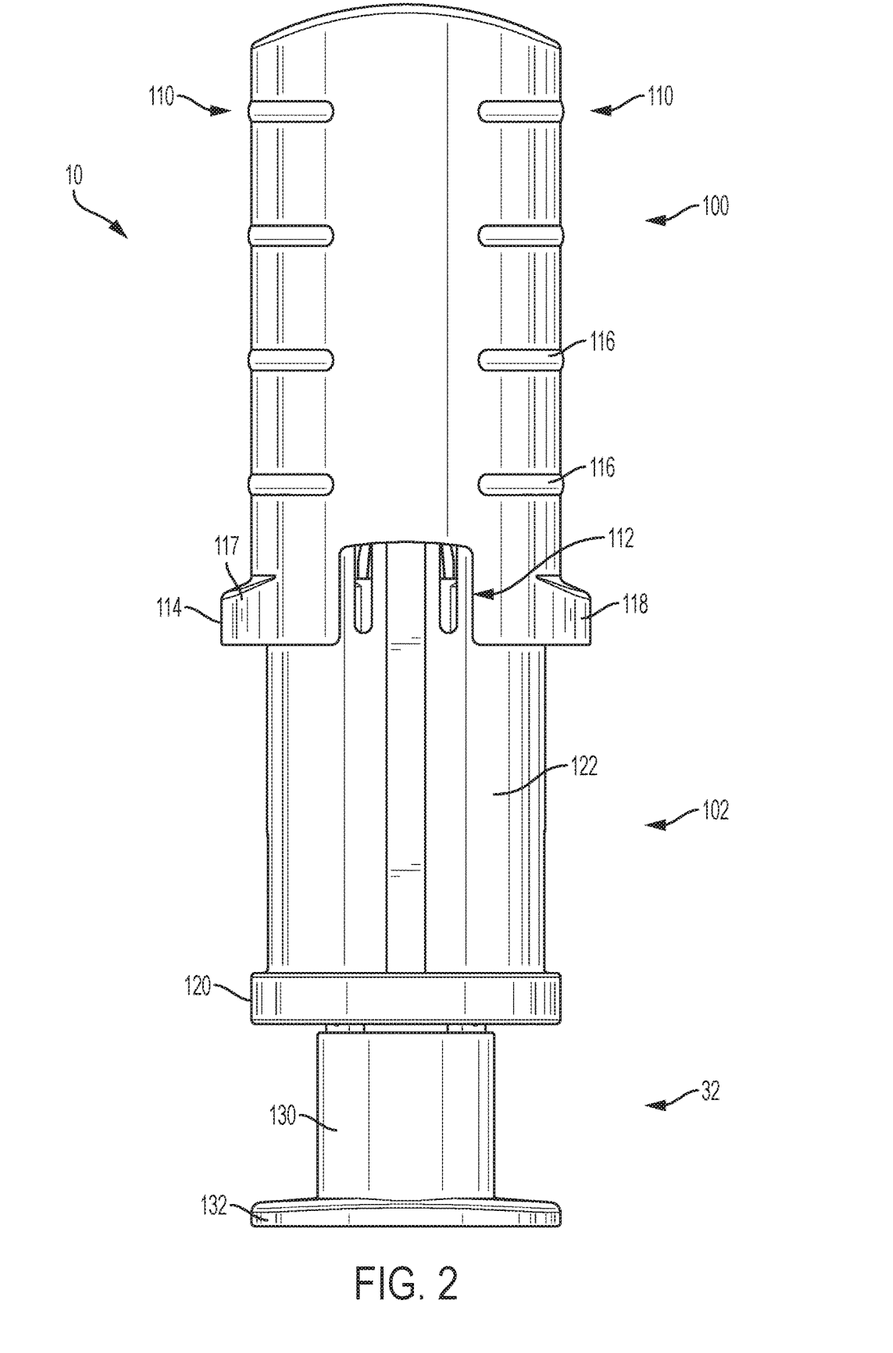
FIG. 2 is a first elevation view of a medical injector in accordance with an embodiment of the present invention.
Figure 3:
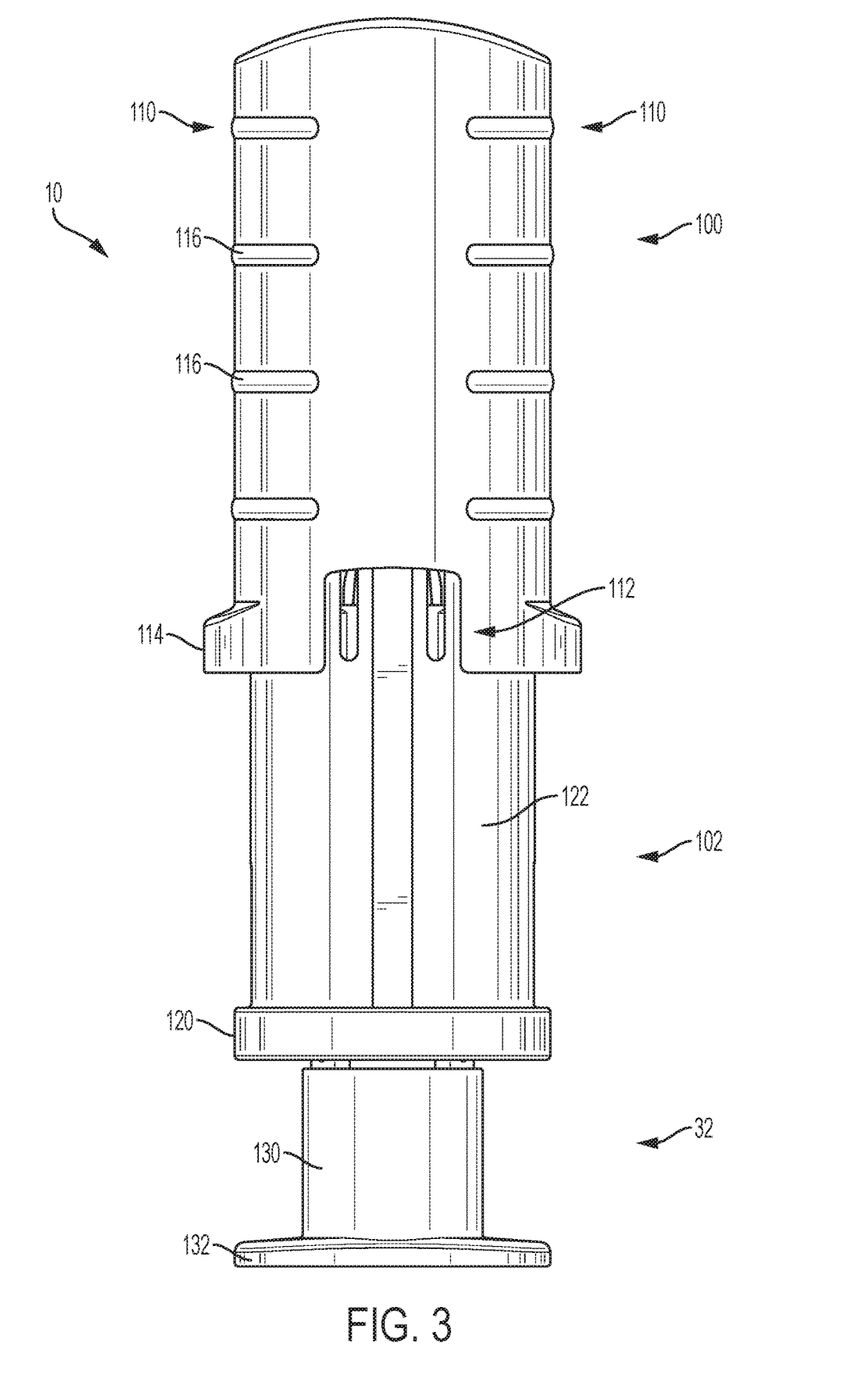
FIG. 3 is a second elevation view of a medical injector in accordance with an embodiment of the present invention.
Figure 4:
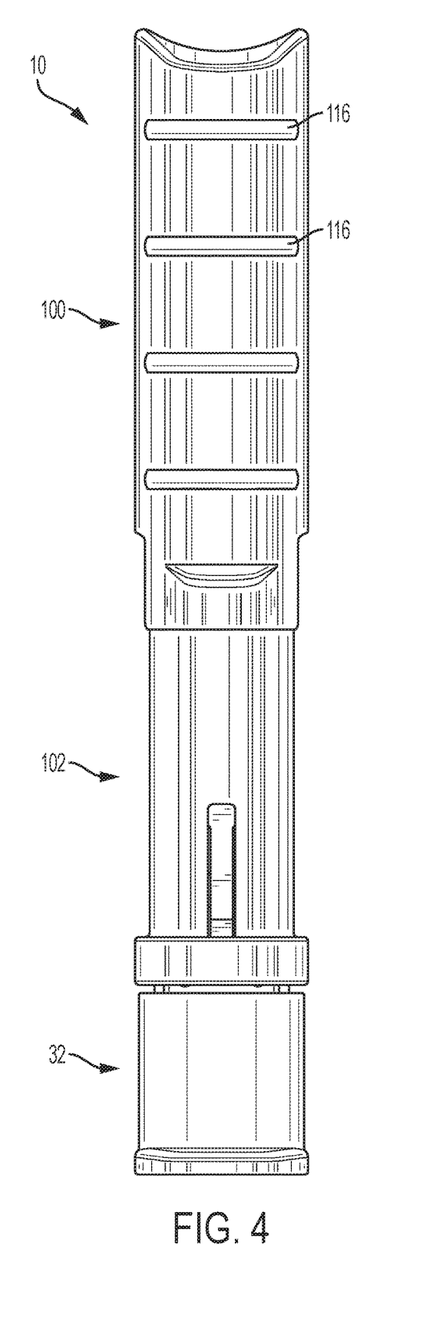
FIG. 4 is a third elevation view of a medical injector in accordance with an embodiment of the present invention.
Figure 5:
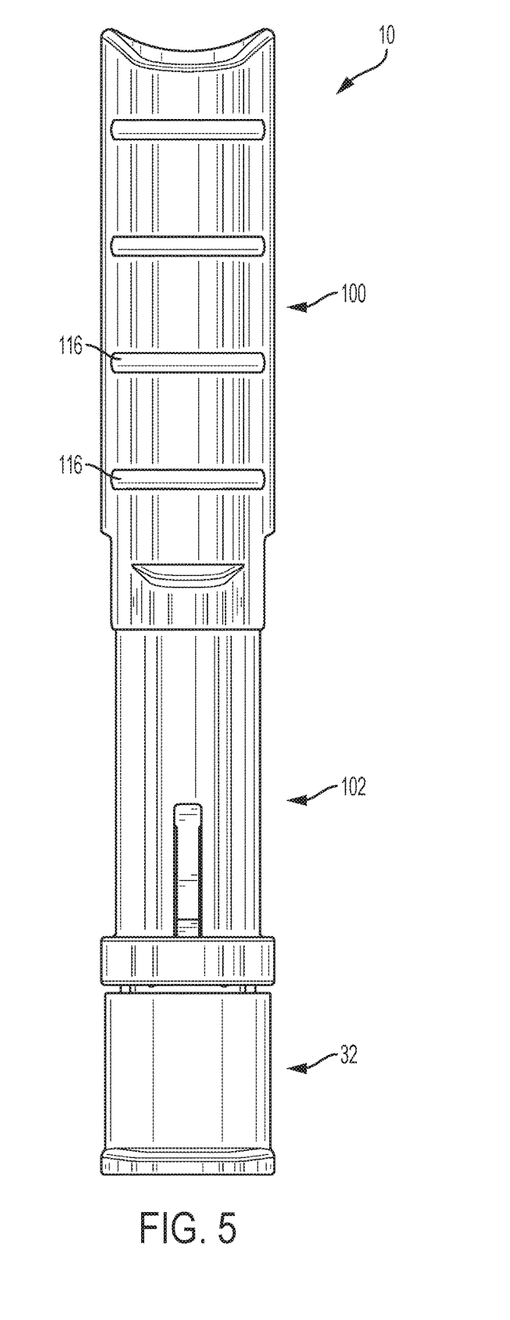
FIG. 5 is a fourth elevation view of a medical injector in accordance with an embodiment of the present invention.
Figure 6:
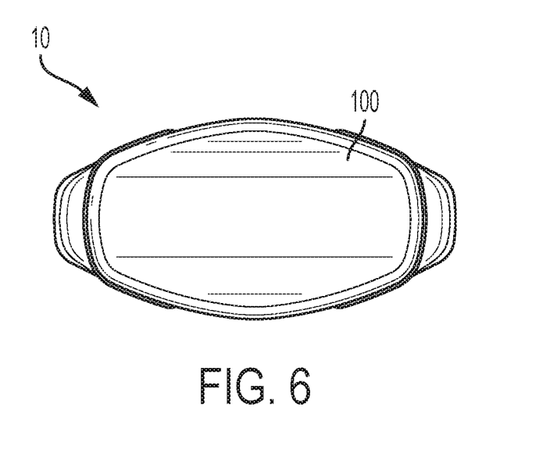
FIG. 6 is a fifth elevation view of a medical injector in accordance with an embodiment of the present invention.
Figure 7:
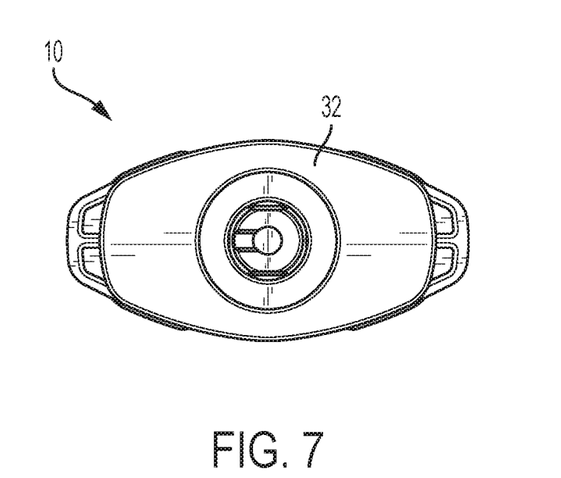
FIG. 7 is a sixth elevation view of a medical injector in accordance with an embodiment of the present invention.
Figure 8:
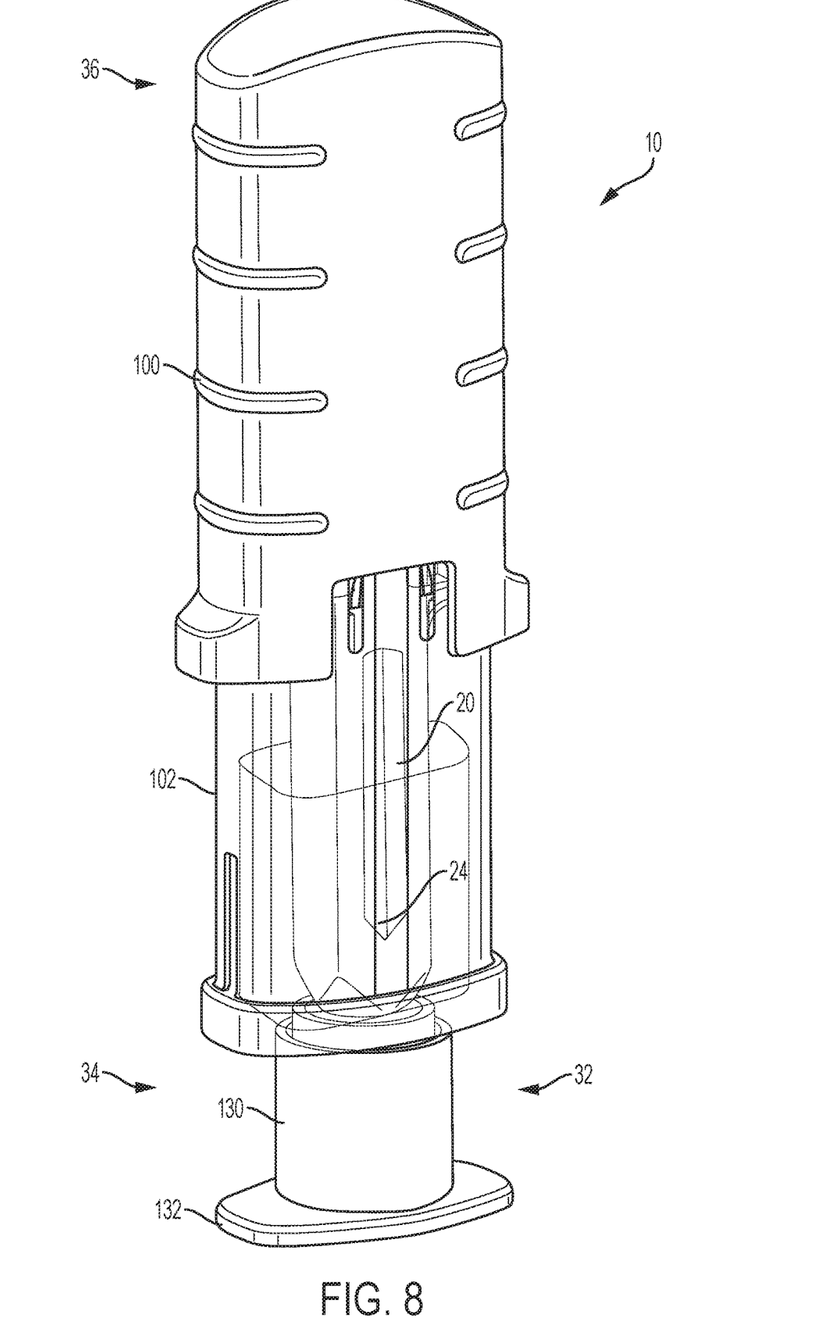
FIG. 8 is a perspective view of a medical injector in accordance with an embodiment of the present invention.
Figure 9:
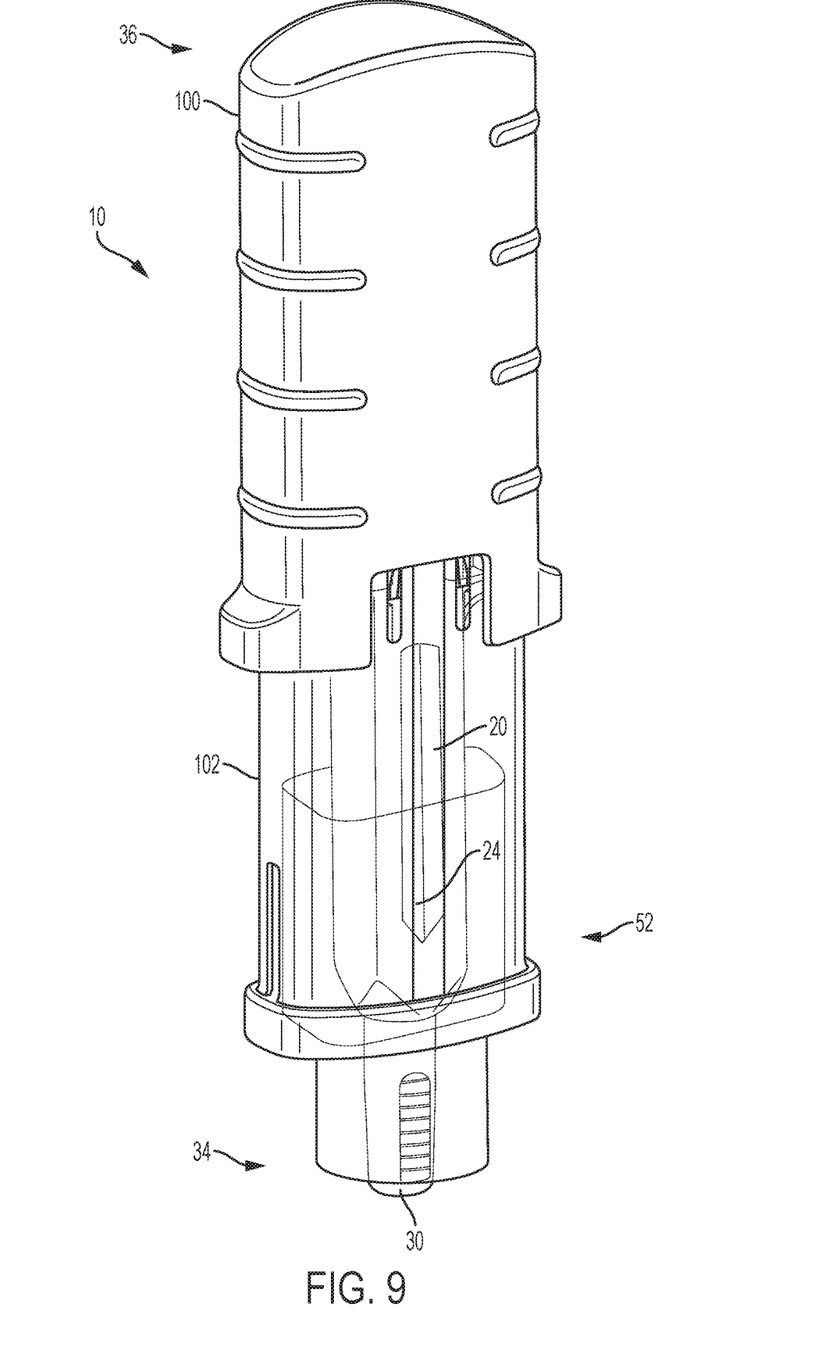
FIG. 9 is a perspective view of a medical injector in accordance with an embodiment of the present invention.

In one embodiment, the medical injector 10 may include a first cap 30 and a second cap or cap remover 32. For example, the second cap 32 can be secured to the medical injector 10 such that the second cap or cap remover 32 shields and covers a distal end 50 of a needle 14 and the first cap 30. Referring to FIG. 9, the first cap 30 shields and covers a distal end 50 of a needle 14. The first cap 30 may be formed of a plastic and/or rubber guard material. In one embodiment, the second cap 32 may be the only cap that shields and covers the distal end 50 of the needle 14.

In one embodiment, with the first cap 30 covering the distal end 50 of the needle 14 and with the second cap 32 covering the distal end 50 of the needle 14 and the first cap 30, the second cap 32 is engaged with the first cap 30 such that removal of the second cap 32 simultaneously removes the first cap 30 from the distal end 50 of the needle 14.

Referring to FIGS. 1-10, a medical injector 10 of the present disclosure includes an upper guard housing component 100 and a lower guard housing component 102. The medical injector 10 includes a body having a distal end 34 and a proximal end 36 extending along a longitudinal axis L. A cross section of the medical injector 10 taken perpendicular to the longitudinal axis L is non-circular in shape. For example, a cross section of the medical injector 10 may be generally elliptical in shape.

In one embodiment, the upper guard housing component 100 includes a gripping component 110, a viewing window 112, and a guard or flange 114. In one embodiment, the gripping component 110 includes gripping ribs 116. In one embodiment, the gripping component 110 includes convex or concave details. The gripping ribs 116 provide a gripping component that includes surfaces for accommodating a user's fingers. For example, the gripping ribs 116 provide ergonomically shaped surfaces that substantially conform to a user's fingertips to aid the user in handling and grasping the medical injector 10. The gripping ribs 116 circumferentially extend at least partially about an exterior surface of the upper guard housing.

The gripping ribs 116 improve the grip between the medical injector 10 and the user's fingertips. In one embodiment, the gripping ribs 116 are integrally formed with the upper guard housing component 100 and provide a visual and tactile cue to the user to instruct the user where to place his or her fingertips.

The upper guard housing component 100 includes a viewing window 112 that allows a user to be able to see a stopper 24 to improve control of the medical injector 10. Accordingly, in one embodiment, the lower guard housing component 102 is formed of a transparent material. In this manner, a user can look through the viewing window 112 and is able to see the stopper 24.

The upper guard housing component 100 includes a guard or flange 114. In one embodiment, the flange 114 includes a first wing flange 117 and a second wing flange 118. The first wing flange 117 and the second wing flange 118 extend in generally opposite directions from the upper guard housing component 100. A proximal surface of each of the first wing flange 117 and the second wing flange 118 may be rounded or tapered for accommodating a user's fingers. The upper guard housing component 100, and more particularly, the flange 114, provides a visual and tactile cue to the user to instruct the user where to place his or her fingertips. For example, the guard 114 prevents a user from handling the medical injector 10 at a position too low.

In one embodiment, the upper guard housing component 100 is moveable relative to the lower guard housing component 102 to advance the stopper 24 to expel a medicament out through the needle 14. As used herein, a stopper 24 refers to a stopper assembly which may include a plunger, a stopper, or a combination thereof, for expelling the medicament from the medical injector 10. In one embodiment, the stopper 24 is permanently affixed within a cavity 103 defined in a distal end of the upper guard housing. Alternatively, the stopper 24 may be secured therein via a variety of well-known securement methods. The upper guard housing component 100 acts a drive member or actuation member for the medical injector 10.

In one embodiment, the lower guard housing component 102 includes a lower guard or lower flange 120 and a transparent body 122. In one embodiment, the lower guard housing component 102 defines a reservoir 20 and a liquid medicament is disposed within the reservoir 20. The transparent body 122 provides a user with visual control of the medical injector 10 during an injection procedure. The lower guard or lower flange 120 keeps an appropriate distance between the hand of a user and a skin surface of a patient during an injection procedure. For example, during an injection, as the upper guard housing component 100 moves distally with respect to the lower housing component 102, the lower guard flange 120 will engage the upper guard flange 114, thereby limiting the distal movement of the upper guard housing component 100 and the user's hand.

The medical injector 10 also includes a needle assembly 12 having a needle 14, the reservoir 20 for medicament sealed by a septum 22, a stopper 24, a first cap 30, and a second cap or a cap remover 32. In one embodiment, the stopper 24 is engaged with a portion of the upper guard housing component 100 and is slidably disposed within the reservoir 20. The stopper 24 is sized to provide sealing engagement with an interior sidewall of the lower guard housing component 102.

The medical injector 10 includes a distal end 34 and a proximal end 36. In one embodiment, the reservoir 20 may be defined by the lower guard housing component 102. In another embodiment, the reservoir 20 may be defined by a separate component contained within the lower guard housing component 102, e.g., a cartridge or barrel. The needle assembly 12 includes a needle 14 and a hub 38. The needle 14 includes a distal end 50, formed for insertion into a patient, and a proximal end 52.

The medical injector 10 of the present disclosure may be of various forms, including being a syringe, self-injector, auto-injector, or pen injector. In one embodiment, the medical injector 10 is well-suited for administering at least one fixed dose. In another embodiment, the medical injector 10 is well-suited for administering a series of fixed doses. The medical injector 10 may be configured such that the upper guard housing component 100 is moveable relative to the lower guard housing component 102 to advance the stopper 24 to expel a medicament out through the needle 14. The medical injector 10 may include a reservoir 20 for accommodating an injectable medicament, which may be a drug cartridge or formed directly in the medical injector 10. The reservoir 20 may have one or more stoppers 24 associated therewith.

Referring to FIG. 9, a first cap 30 shields and covers the distal end 50 of the needle 14. In one embodiment, the second cap or cap remover 32 shields and covers the distal end 50 of the needle 14 and the first cap 30. In one embodiment, the second cap 32 may be the only cap that shields and covers the distal end 50 of the needle 14.

Referring to FIGS. 1-8, the second cap or cap remover 32 includes a cylindrical portion 130 and a distal flange 132.

In one embodiment, with the first cap 30 covering the distal end 50 of the needle 14 and with the second cap 32 covering the distal end 50 of the needle 14 and the first cap 30, the second cap 32 is engaged with the first cap 30 such that removal of the second cap 32 simultaneously removes the first cap 30 from the distal end 50 of the needle 14.

In one embodiment, the second cap 32 provides a gripping component that includes surfaces for accommodating a user's fingers, such as distal flange 132 or similar structure. For example, the distal flange 132 of the second cap 32 provides ergonomically shaped surfaces that substantially conform to a user's fingertips to aid the user in removing the second cap 32 from the distal end 50 of the needle 14 and/or to aid the user in simultaneously removing the second cap 32 and the first cap 30 from the distal end 50 of the needle 14. The distal flange 132 of the second cap 32 provides a user with multiple finger grip positions for the user. For example, the distal flange 132 of the second cap 32 allows a user to handle and/or grip the second cap 32 in a variety of different ways. In one embodiment, the shape of the second cap 32 is designed to help disabled people more easily and more conveniently handle the second cap 32 and/or the medical injector 10.

In one embodiment, the distal flange 132 of the second cap 32 allows a user to handle the second cap 32 without finger flexion. In one embodiment, the distal flange 132 of the second cap 32 provides a gripping component that allows a user to better handle the second cap 32 and/or the medical injector 10.

Figure 10:
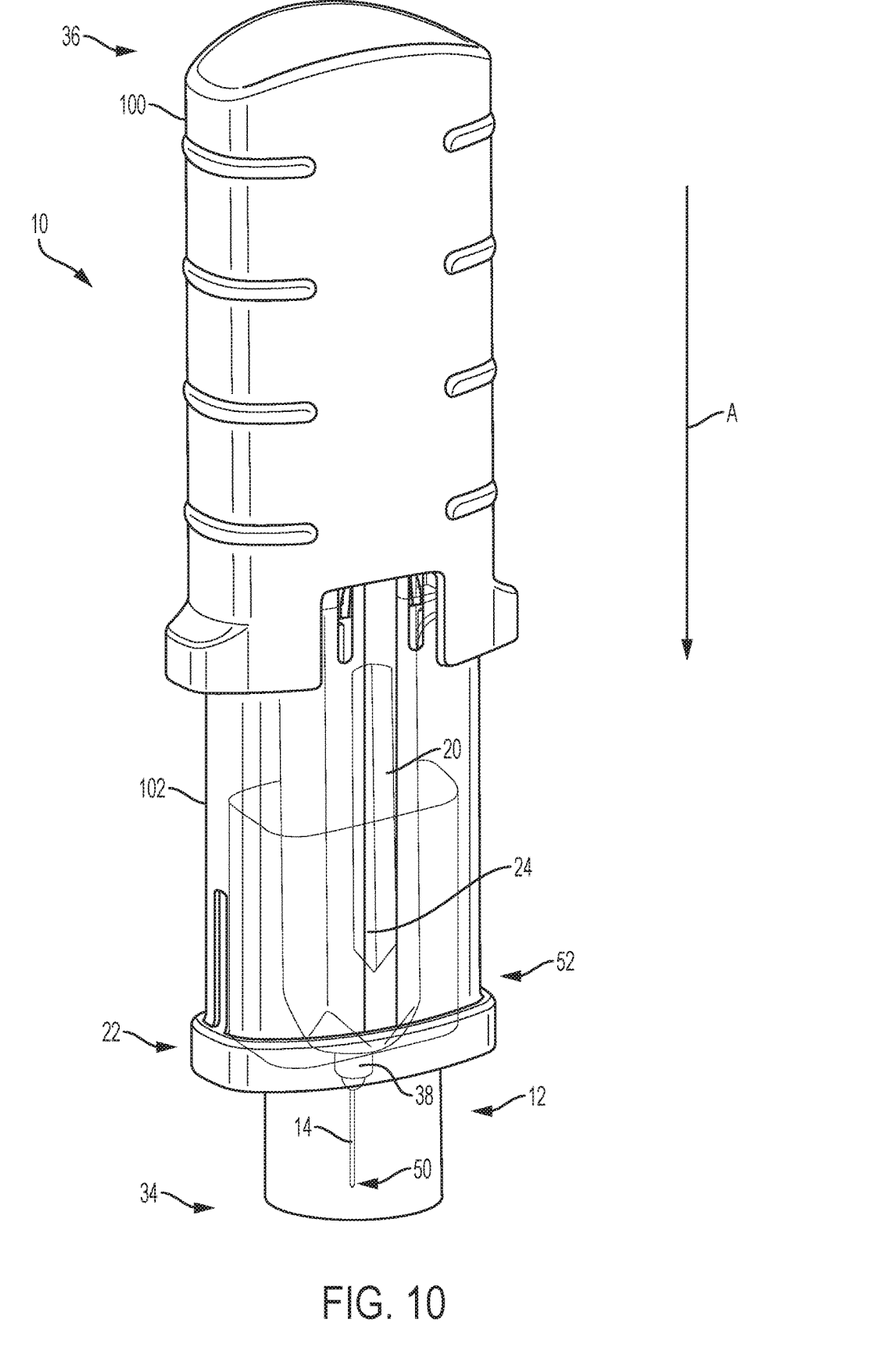
FIG. 10 is a perspective view of a medical injector in accordance with an embodiment of the present invention.

When it is desired to use the medical injector 10 of the present disclosure, in one embodiment, the second cap 32 is used to easily remove the second cap 32 and the first cap 30 from the distal end 50 of the needle 14 simultaneously. Referring to FIG. 10, with the caps 30, 32 removed, the distal end 50 of the needle 14 is exposed and ready to be positioned adjacent a desired portion of the skin of a user.

When it is desired to expel or deliver the medication contained within the reservoir 20 of the medical injector 10, and with the medical injector 10 properly used to contact and pierce the skin of a user, the upper guard housing component 100 can be moved in a direction generally along arrow A (FIG. 10) to advance the stopper 24 and to expel a medicament out through the needle 14.

Movement of the upper guard housing component 100 in the direction generally along arrow A actuates movement of the stopper 24 in the direction generally along arrow A toward the distal end 34 of the medical injector 10. In this manner, movement of the stopper 24 in the direction generally along arrow A forces the medicament fluid contained within the reservoir 20 to be forced out the distal end 50 of the needle 14 and into the user and/or patient.

After injection of the medicament fluid, the needle 14 can be removed from the skin of the patient. In one embodiment, the medical injector 10 may include an automatic retraction mechanism for moving the needle 14 into the medical injector 10 for safe shielding of the needle 14 after use. In one embodiment, a spring may be used as part of the automatic retraction mechanism.

All of the components of the medical injector 10 may be constructed of any known material, and are desirably constructed of medical-grade polymers.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A medical injector comprising:
   an upper guard housing including a gripping component;
   a lower guard housing defining a reservoir and having a flange provided on a portion of the lower guard housing;
   a stopper engaged with a portion of the upper guard housing and slidably disposed within the reservoir, the stopper sized to provide sealing engagement with an interior sidewall of the lower guard housing;
   wherein the upper guard housing at least partially surrounds the lower guard housing and is moveable relative to the lower guard housing during an injection to advance the stopper through the reservoir,
   wherein distal movement of the upper guard housing relative to the lower guard housing during the injection is limited by engagement of the upper guard housing with the flange of the lower guard housing.

2. The medical injector of claim 1, wherein the gripping component is concave or convex with respect to an exterior surface of the upper guard housing.

3. The medical injector of claim 2, wherein the gripping component comprises a plurality of gripping ribs extending at least partially about the exterior surface of the upper guard housing.

4. The medical injector of claim 1, wherein a window is defined through a portion of the upper guard housing for viewing the stopper during use.

5. The medical injector of claim 1, wherein the lower guard housing component comprises a transparent material.

6. The medical injector of claim 1, further comprising a flange provided adjacent a distal end of the upper guard housing.

7. The medical injector of claim 1, wherein a cross section of the upper guard housing taken perpendicular to a longitudinal axis of the upper guard housing is generally elliptical in shape.

8. The medical injector of claim 1, further comprising a needle having a sharpened first end and a second end in communication with the reservoir.

9. The medical injector of claim 8, further comprising a liquid medicament disposed within the reservoir.

10. The medical injector of claim 9, further comprising a cap covering the sharpened first end of the needle.

11. A handle component for use with a medical injection device for dispelling a fluid from the medical injection device, the handle comprising:
    a handle body having a proximal end, a distal end, and an interior wall defining a cavity within the distal end of the handle body;
    a stopper assembly receivable at least partially within the cavity; and
    a gripping component provided on an external surface of the handle body,
    wherein the handle body is adapted to be mounted over a housing defining a reservoir and axially slidable over the housing during an injection to advance the stopper through the reservoir,
    wherein the distal end of the handle body is configured engage a flange of the housing to limit distal movement of the handle body relative to the housing during the injection.

12. The handle component of claim 11, wherein the gripping component comprises a plurality of ribs, the ribs being convex with respect to the handle body.

13. The handle component of claim 11, wherein the handle body comprises a non-circular cross section taken perpendicular to a longitudinal axis of the handle body.

14. The handle component of claim 13, wherein the cross section is substantially elliptical in shape.

15. The handle component of claim 11, wherein a window is defined through a portion of the handle body.

16. The handle component of claim 11, wherein a flange is provided adjacent the distal end of the handle body.

17. The handle component of claim 16, wherein the flange comprises a first wing flange extending from the handle body in a first direction and a second wing flange extending from the handle body in a second direction, wherein the first direction is generally opposite the second direction.

18. The handle component of claim 17, wherein the first wing flange and second the second wing flange each comprise a tapered proximally directed surface.

\* \* \* \* \*

UNITED STATES PATENT AND TRADEMARK OFFICE
CERTIFICATE OF CORRECTION

PATENT NO. : 10,737,036 B2
APPLICATION NO. : 15/372591
DATED : August 11, 2020
INVENTOR(S) : Jean-Yves Corbin et al.

Page 1 of 1

It is certified that error appears in the above-identified patent and that said Letters Patent is hereby corrected as shown below:

In the Claims

Column 8, Line 9, Claim 11, after "configured" insert -- to --

Column 8, Line 31, Claim 18, after "and" delete "second"

Signed and Sealed this
Twenty-second Day of December, 2020

Andrei Iancu
*Director of the United States Patent and Trademark Office*